United States Patent [19]

Rautsola

[11] Patent Number: 4,826,500

[45] Date of Patent: May 2, 1989

[54] ENTERAL NUTRIENT DELIVERY SYSTEM

[76] Inventor: Riku H. Rautsola, Gerhart-Hauptmann Str. 4, 6370 Oberursel, Fed. Rep. of Germany

[21] Appl. No.: 109,230

[22] Filed: Oct. 16, 1987

[51] Int. Cl.4 .......................... A61J 3/00; A61M 5/00; B67B 7/26

[52] U.S. Cl. ........................................ 604/411; 272/91

[58] Field of Search ......................... 604/251, 411-414, 604/405, 406; 222/81, 91

[56] References Cited

U.S. PATENT DOCUMENTS

| | | | |
|---|---|---|---|
| 2,177,874 | 10/1939 | Norza | 222/91 |
| 3,549,049 | 12/1970 | Weber | 222/91 |
| 3,662,752 | 5/1972 | Yokoyama | 604/411 |
| 3,973,698 | 8/1976 | Kato | 222/91 |
| 4,655,763 | 4/1987 | Malcolm et al. | 604/411 X |

*Primary Examiner*—Dalton L. Truluck
*Attorney, Agent, or Firm*—Kinney & Lange

[57] ABSTRACT

A system for the enteral delivery of a solution, including desired nutrients to a human. The solution is passed from a container through an elongated giving set and metering system into a nasal tube. In accordance with the present invention, the container is an aseptic carton having penetrable side walls while the giving set terminates at a fitting having a fluid passage extending therethrough. The fitting terminates at a carton cooperating portion which includes a first portion for penetrating the carton side walls to form an orifice therein, the orifice establishing fluid communication between the carton interior and the fitting fluid passage, and a second portion for engaging the carton side wall to maintain cooperating between the carton and fitting. A seal is provided to block fluid flow from the carton interior except through the fluid passage while, in a preferred embodiment, provision is made for the delivery of make-up air to the interior of the carton.

3 Claims, 1 Drawing Sheet

ENTERAL NUTRIENT DELIVERY SYSTEM

BACKGROUND OF THE INVENTION

1. Field of the Invention.

Aseptic packaging is finding increasing acceptance for various liquids. For example, such packaging is commonly employed for fruit juices and milk products. Additionally, such packaging has been employed for medical solutions such as those employed during enteral (as opposed to intravenous) feeding. The present invention relates to the latter and, more particularly, to a system for the delivery of a solution from an aseptic package for enteral application, as by nasal gauge.

2. Description of the Prior Art.

For the purposes of the present specification and claims, the term "aseptic packaging" is intended to embrace the packaging of various liquids within a carton, the carton being of the type that is punctured to gain access to the packaged liquid. When the packaged liquid is a food product, such as juices or milk products, it is common to puncture the packaging, at a preselected location, and withdraw the liquid through a straw. In Europe, it is known to provide a "tap" which is pointed such that it may be employed to puncture a side wall of the packaging and which has a fluid passage allowing the contained liquid to be poured through the tap.

The characteristics of the noted packaging systems render their use desirable in many medical applications. For example, it is often desirable or necessary to deliver liquids to a person by a nasal tube for such purposes as enteral feeding, the delivery of nutrients, the delivery of medication, etc. Aseptic packaging is often suitable for such liquids. However, typical packaging techniques employed to form such packaging have limited the amount of liquid that may be contained within the packaging. For example, many known prior art packaging machines cannot handle liquid quantities in excess of approximately ½ liter. Thus, while aseptic packaging has been employed for certain medical solutions, it has often been the practice to open the packages and empty their contents into a more traditional container for enteral delivery of the solution, as by nasal gauge. More recent packaging techniques do allow the packaging of liquid quantities in the one liter. Further, the tap, described above in the context of food products, has the drawback of not discharging the liquid in an even flow but, instead, discharges the contents of the package intermittently so as to allow air to enter the container through the tap.

SUMMARY OF THE INVENTION

The present invention provides a system for the enteral delivery of a solution contained within an aseptic package (without the intervening step of emptying the package into a traditional container) for dispensing through a giving set and metering system and, typically, via a tube as by nasal gauge. In accordance with the present invention, the solution is contained within an aseptic carton having penetrable side walls with the giving set terminating at a fitting having a fluid passage extending therethrough. The fitting terminates at a carton cooperating portion including a first carton penetrating portion, a portion which engages the carton side wall and a seal for preventing leakage of the contained fluid liquid from around the fitting. Provision is also made for make-up air such that an even outflow of liquid is attained. In operation, the carton penetrating portion of the fitting establishes an orifice through the side wall of the carton with the orifice establishing fluid communication between the carton interior and a fluid passage through the fitting. The fitting is on the fitting which engage the orifice opening. A particle filter may also be employed to maintain the aseptic condition of the carton interior.

DETAILED DESCRIPTION OF THE PREFERRED EMBODIMENTS

Figure 1:
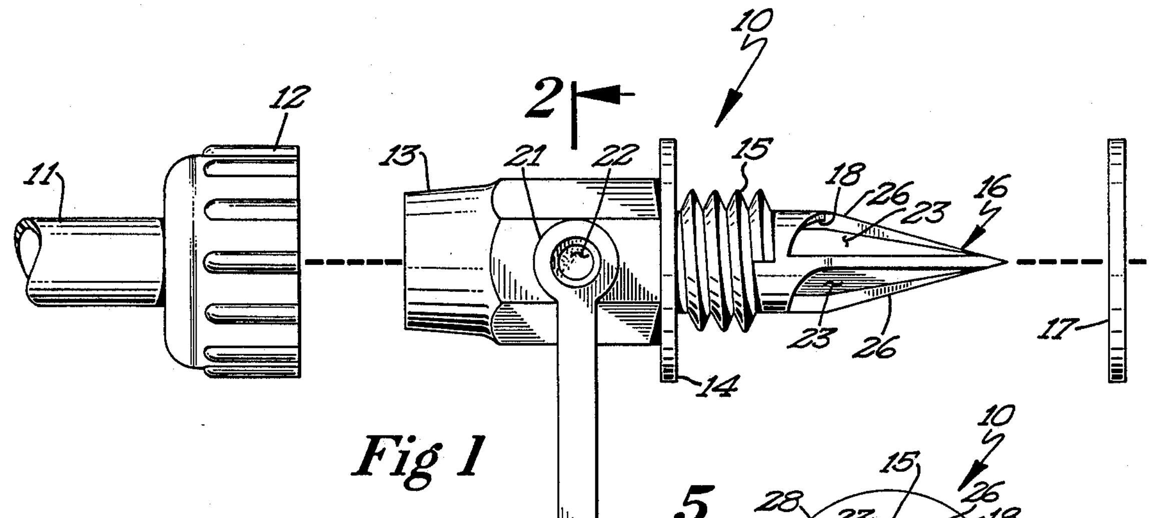
FIG. 1 is an exploded view illustrating a preferred embodiment of the present invention.

FIG. 1 is an exploded view of a system in accordance with the present invention including a fitting designated generally at 10, the fitting 10 being adapted for connection to an elongated tubing 11. The tubing 11 represents a delivery system for a solution which is desired to be introduced into a human body which typically includes a "giving set" as well as a metering system. Tubing 11 is secured within a cap 12, the cap 12 being fixed to the fitting 10 as by gluing it to a collar 13. The fitting 10 illustrated in the several views of the drawing figures is particularly adapted for use with aseptic packaging of a type having penetrable side walls.

As described more fully below, the packaging cooperating portion of the fitting 10 includes a shoulder 14, threaded portion 15 and a package penetrating portion 16. A central passageway extends through the collar 13 to the penetrating portion 16 to allow for an outflow of solution from the packaging to and through the giving set represented by the tubing 11. A washer 17 is adapted to fit over the penetrating portion 16 and threaded portion 15 to overlie the shoulder 14 to be compressed against the side wall of the packaging to provide a seal against leakage of the solution contained within the packaging.

Figure 2:
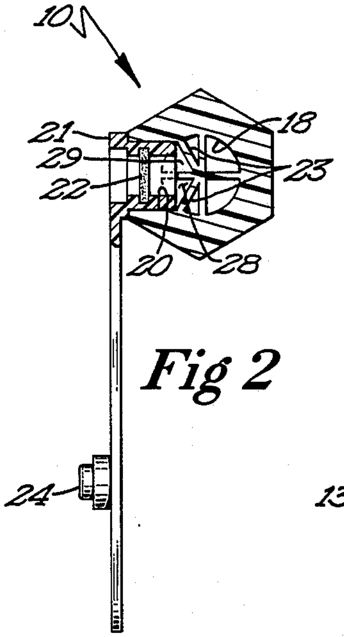
FIG. 2 is a cross section taken along line 2—2 in FIG. 1.
Figure 4:
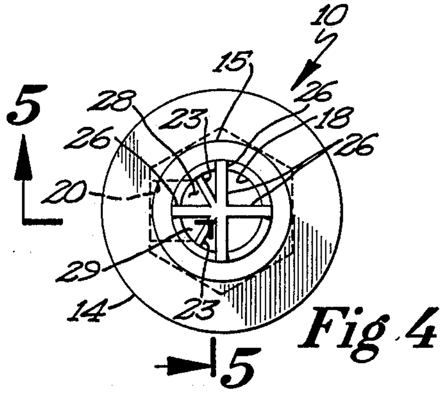
FIG. 4 is an end view of a fitting portion illustrated in FIG. 3.

FIG. 2 illustrates a cross section taken along the line 2—2 of FIG. 1 including the central passageway 18. An aperture 20 in the body of the fitting 10 (see FIG. 3) is provided with an insert 21, the insert 21 containing a molecular filter media 22 of a type known to the prior art. As will be described more fully below, the air inlet allows a flow of make-up air from the surroundings to enter the interior of the carton containing the solution being dispensed, thereby providing an even outflow of that liquid. The filter 22 is of the type known to the prior art and may be selected to exclude particles in any desired size. Typically, the filter 22 is also a one-way membrane which will allow an inflow of air but block an outflow such as an outflow of liquid passing through the passageway 18. Baffles 23 (described more fully below) define a distinct air passageway within the passageway 18. A plug 24 may be provided to close the air inlet 21.

Figure 3:
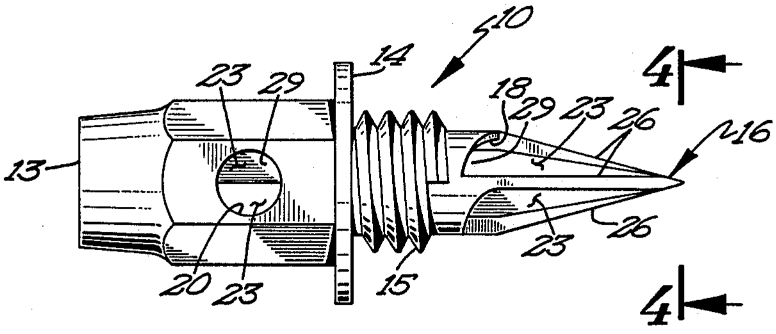
FIG. 3 is a side view of the primary component of the fitting of the present invention.
Figure 5:
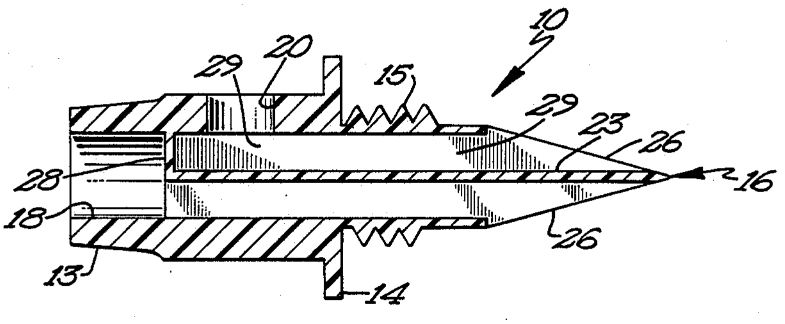
FIG. 5 is a cross section taken along line 5—5 in FIG. 4.

FIG. 3 illustrates body portion 10 of the fitting in accordance with the present invention. As illustrated in FIGS. 1 and 3, the pentrating portion 16 is formed of wedge-shaped members 26 extending from the threaded portion 15. At least two of the wedge-shaped members 26 extend into the passageway 18, those extensions being shown at 23 within the passageway 18 in FIG. 2, and in FIG. 5. As also shown in FIG. 5, an end wall 28 may be provided to fully block off a passageway 29 defined by the walls 23 (the extensions of the wedges 26) to isolate the passageway 29 from the passageway 18.

In use, the collar 13 and cap 12 will be secured to each other, as by gluing, and the plug 24 will be closing the air inlet by insertion within the insert 21. The penetrating portion 16, formed of wedges 26, will be inserted through the side wall of an aseptic package to form an orifice therein for the passage of fluid from the carton interior and through the passageway 18. The threads 15 will engage the edges of the orifice and, on rotation of the fitting 10, will bring the shoulder 14, and the washer 17 which overlies the shoulder 14, into engagement with the side wall of the carton. Compression of the washer 17 will provide a seal of the carton orifice to block liquid flow from the orifice except through the fluid passage 18. By removing the plug 24 from the insert 21, the air inlet is opened and the passageway 29 will provide a passage for make-up air into the carton interior as the liquid in the container exits that container through the passageway 18. Thus, a steady outflow of liqiud is provided from the carton interior for delivery by the giving set to an appropriate metering system, if desired. In essence, the use of the fitting 10, in combination with an aseptic packaging described herein, facilitates the use of that packaging without alteration of the giving set and metering system, with the exception of the use of the fitting in accordance with the present invention.

Obviously, many modifications and variations of the present invention are possible in light of the above teachings. It is therefore to be understood that, within the scope of the apended claims, the invention may be practiced otherwise than as specifically described.

What is claimed is:

1. In a closed system for the enteral delivery of a solution, including desired nutrients, to a human of the type wherein the solution is passed from a container through an elongated giving set and metering system, the improvement wherein the container comprises an aseptic carton having penetrable side walls, said giving set terminating at a fitting having a fluid passage extending therethrough and terminating at a carton cooperating portion, the carton cooperating portion including:

means for penetrating the carton side wall to form an orifice therein including projecting wedge-shaped members extending from said fluid passage, at least two of said wedge-shaped members extending into said fluid passage and defining an air passage isolated from and located within said fluid passage for passing make-up air for the interior of the carton, said orifice establishing fluid communication between the carton interior and said fitting fluid passage;

air inlet means communicating with said air passage;

means for engaging the carton side wall to maintain said fluid communication including a threaded portion around said fluid passage; and means for blocking fluid flow from said orifice except through said fluid passage.

2. The system of claim 1 wherein said fluid flow blocking means comprises shoulder means around said carton cooperating portion and sealing means overlying said shoulder means.

3. The system of claim 1 further comprising particle filter means within said air inlet means.

* * * * *